(12) United States Patent
Packirisamy et al.

(10) Patent No.: US 9,863,825 B2
(45) Date of Patent: Jan. 9, 2018

(54) SYSTEM FOR SENSING A MECHANICAL PROPERTY OF A SAMPLE

(71) Applicants: Muthukumaran Packirisamy, Pierrefonds (CA); Roozbeh Ahmadi, Nepan (CA); Javad Dargahi, Lasalle (CA)

(72) Inventors: Muthukumaran Packirisamy, Pierrefonds (CA); Roozbeh Ahmadi, Nepan (CA); Javad Dargahi, Lasalle (CA)

( * ) Notice: Subject to any disclaimer, the term of this patent is extended or adjusted under 35 U.S.C. 154(b) by 0 days.

(21) Appl. No.: 15/163,264

(22) Filed: May 24, 2016

(65) Prior Publication Data

US 2016/0265989 A1 Sep. 15, 2016

Related U.S. Application Data

(63) Continuation-in-part of application No. 13/881,673, filed as application No. PCT/CA2011/001192 on May 2, 2013, now abandoned.

(Continued)

(51) Int. Cl.
*A61B 34/30* (2016.01)
*G01L 1/24* (2006.01)
(Continued)

(52) U.S. Cl.
CPC .............. *G01L 1/242* (2013.01); *A61B 34/30* (2016.02); *G01B 11/18* (2013.01); *G01D 5/268* (2013.01); *G01D 5/353* (2013.01)

(58) Field of Classification Search
CPC ... G01L 1/242; G01L 1/18; G01L 1/24; G01L 1/243; G01L 1/16; G01D 5/353;
(Continued)

(56) References Cited

U.S. PATENT DOCUMENTS 4,159,640 A 7/1979 Leveque et al.
4,651,074 A 3/1987 Wise
(Continued)

FOREIGN PATENT DOCUMENTS

WO 2009127071 A1 10/2009
WO WO 2009127071 A1 * 10/2009 ............... G01N 3/40

OTHER PUBLICATIONS

Ashkan Mirbagheri et al., "Mathematical Modeling of a Tactile Sensor with Applications in Minimally Invasive Surgery", American Journal of Applied Sciences, Oct. 2007, vol. 4 (Issue 10), pp. 779-785.
(Continued)

*Primary Examiner* — Laura Martin
*Assistant Examiner* — Suman K Nath

(57) ABSTRACT

A sensing element for sensing a mechanical property of a sample defining a sample surface using a contact force exerted the sample surface. The sensing element includes: a deformable element defining a contact surface and a deformable section in register with the contact surface, the deformable section being deformable between an undeformed configuration and a deformed configuration; a deformation sensor operatively coupled to the deformable section for sensing and quantifying a deformation of the deformable section between the deformed and undeformed configurations, the deformation sensor being an optical deformation sensor; and a force sensor operatively coupled to the deformable element for sensing the contact force exerted on the contact surface.

20 Claims, 7 Drawing Sheets

Related U.S. Application Data

(60) Provisional application No. 61/344,859, filed on Oct. 26, 2010.

(51) Int. Cl.
*G01D 5/353* (2006.01)
*G01B 11/16* (2006.01)
*G01D 5/26* (2006.01)
*G01L 1/16* (2006.01)

(58) Field of Classification Search
CPC .......... A61B 19/2203; A61B 2019/465; A61B 2019/2292; A61B 34/30; G01M 11/085
USPC .................................... 73/862.624, 800, 624
See application file for complete search history.

(56) References Cited

U.S. PATENT DOCUMENTS

| | | |
|---|---|---|
| 4,691,708 A | 9/1987 | Kane |
| 4,733,068 A | 3/1988 | Thiele et al. |
| 4,948,219 A * | 8/1990 | Seino ..................... G02B 6/30 |
| | | 385/95 |
| 5,524,636 A | 6/1996 | Sarvazyan et al. |
| 6,663,641 B1 | 12/2003 | Kovac et al. |
| 6,838,660 B2 | 1/2005 | Duncan et al. |
| 6,848,304 B2 | 2/2005 | Geen |
| 7,303,534 B2 | 12/2007 | Kahn |
| 7,707,001 B2 | 4/2010 | Obinata et al. |
| 2003/0176948 A1 | 9/2003 | Green |
| 2004/0129083 A1 | 7/2004 | Fernald et al. |
| 2004/0232201 A1 | 11/2004 | Wenchell et al. |
| 2005/0065426 A1 | 3/2005 | Porat et al. |
| 2005/0102062 A1 | 5/2005 | Green |
| 2005/0131390 A1 | 6/2005 | Heinrich et al. |
| 2005/0262949 A1 | 12/2005 | Schostek et al. |
| 2006/0152885 A1 | 7/2006 | Hewit et al. |
| 2006/0200049 A1 | 9/2006 | Leo et al. |
| 2007/0038152 A1 | 2/2007 | Sarvazyan et al. |
| 2007/0040107 A1 | 2/2007 | Mizota et al. |
| 2007/0177162 A1* | 8/2007 | Glueck ................. F16C 19/522 |
| | | 356/621 |
| 2008/0009750 A1 | 1/2008 | Aeby et al. |
| 2008/0294144 A1 | 11/2008 | Leo et al. |
| 2010/0102034 A1* | 4/2010 | Renz .................... H01H 33/668 |
| | | 218/140 |

OTHER PUBLICATIONS

Dargahi J. et al. "Fabrication and testing of a medical surgical instrument capable of detecting simulated embedded lumps" American Journal of Applied Sciences, Dec. 2007, vol. 4, No. 12, pp. 957-964.

Dargahi J. et al. "Design and microfabrication of a hybrid piezo-electric-capacitive tactile sensor", Sensor Review, Sep. 2006 vol. 26, Issue 3; pp. 186-192.

Dargahi J. et al. "An endoscopic and robotic tooth-like compliance and roughness tactile sensor" Journal of Mechanical Design, Sep. 2002, vol. 124, pp. 576-582.

Dargahi J. et al. "A micromachined piezoelectric tactile sensor for endoscopic grasper: theory, fabrication and experiments", IEEE-ASME Journal of MicroElectroMechanical Systems, Sep. 2000, vol. 9, No. 3, pp. 329-336.

Dargahi J., "A piezoelectric tactile sensor with three sensing elements for robotic, endoscopic and prosthetic applications", Sensors and Actuators A: Physical, Mar. 2000, Vol. 80/1, pp. 23-30.

Entire prosecution history of U.S. Appl. No. 12/988,410 from filing to Sep. 25, 2013; Inventor: Javad Dargahi et al.

* cited by examiner

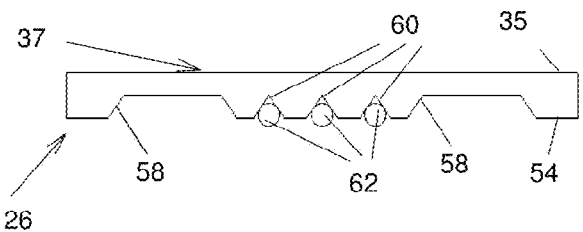
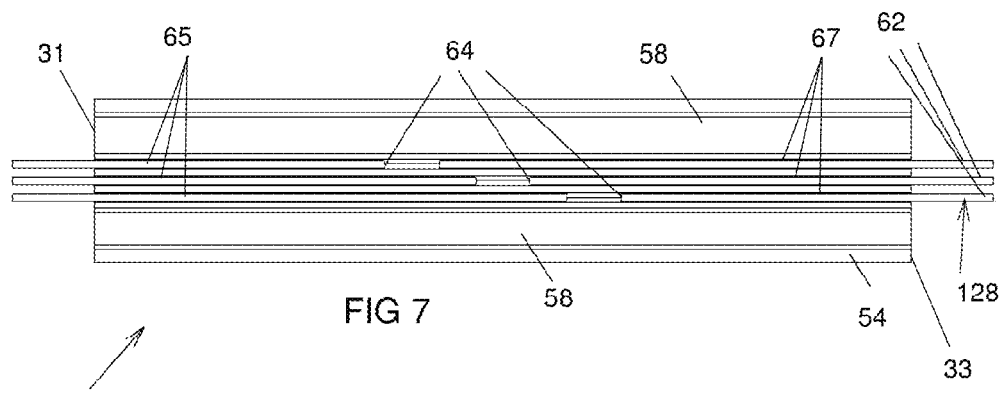
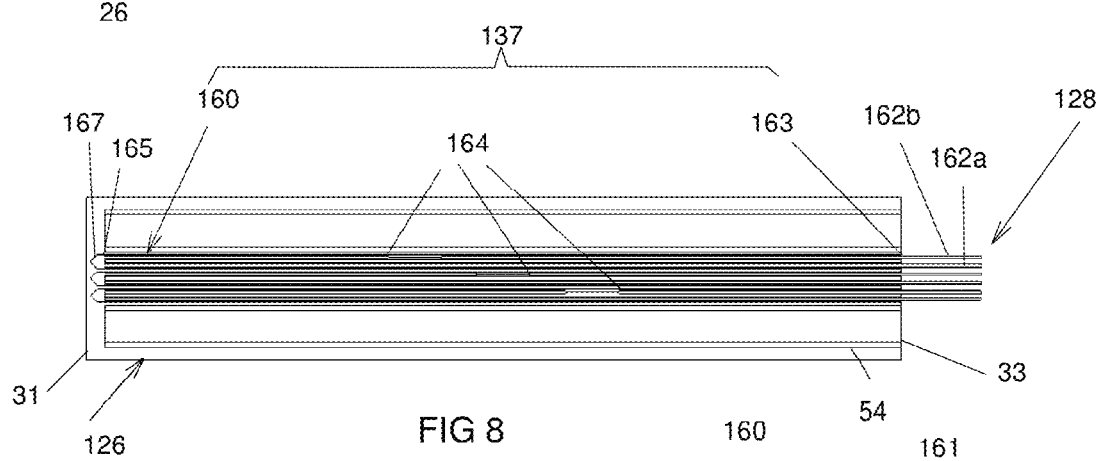
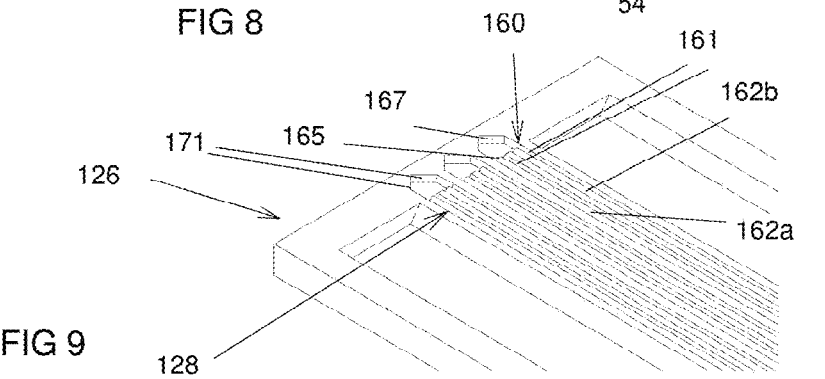

SYSTEM FOR SENSING A MECHANICAL PROPERTY OF A SAMPLE

FIELD OF THE INVENTION

The present invention relates to the art of sensors. More specifically, the present invention is concerned with systems for a mechanical property of a sample. In some embodiments of the invention, the system uses optical components for sensing the deformation of the sample in response to a force exerted thereonto, the force being also measured.

BACKGROUND OF THE INVENTION

In conventional surgery, surgeons use their fingers to measure the softness/hardness of tissues. Using this type of palpation, surgeons can investigate hidden anatomical features of tissues. They can also distinguish between different types of tissues. For example, they can identify abnormal tissues (such as tumorous lumps), blood vessels, ureters, and bony or fatty tissues. However, current commercially available minimally invasive robotic surgery (MIRS) systems do not provide tactile feedback from the interaction between surgical tools and tissues.

Indeed, despite the superiority in many cases of MIRS over conventional open surgery techniques, it has a few unsolved shortcomings. One of them is the lack of haptic feedback to surgeons. Such haptic feedback relies on sensory feedback, which consists of both the kinesthetic and cutaneous tactile feedback streams. Haptic feedback, which occurs while surgical instruments are interacting with tissues, can lead to better MIRS. For instance, visual force feedback results in reduced suture breakage, lower forces, and decreased force inconsistencies in the da Vinci™ surgical system. Similarly, experimental tests have proved that the presence of direct force feedback significantly reduces the force applied by the da Vinci™ graspers to the grasped tissue. That reduced force was not sustainable after removing the force feedback.

Therefore, similarly to a human finger, a tactile sensor is required to measure: 1) the softness/hardness of contact tissue, 2) the contact distributed load interacting between surgical tools and tissues, and 3) the position of a concentrated load interacting between surgical tools and tissues. Also, surgical tool-tissue interactions take place in both static and dynamic loading conditions. In order to avoid tissue damage because of the excessive force applied to the tissue, and also in order to maintain contact stability between surgical tools and tissues, surgeons can use a sensor to measure the static contact force applied to tissues by surgical tools. In addition, tool-tissue interaction involves low rate changes because of the viscoelastic properties of tissues. For example, tissue relaxation happens very slowly. As a result, the tactile sensor must measure the above-mentioned parameters in both static and dynamic loading conditions.

Finally, minimally invasive robotic surgeries are frequently performed in the presence of electro-magnetic fields. Magnetic resonance imaging (MRI) devices induce strong electro-magnetic fields. Nowadays, during MIRS, these devices are in widespread use in surgical rooms for various types of applications. For example, surgeons widely use MRI to investigate the live organs during MIRS. As another example, in MIRS applications, surgeons also use them to guide the surgical instruments and to track the position of surgical tools inside the body. Similarly, radio frequency (RF) pulses are usually present in the surgical operating rooms. For example, RF coil of MRI devices is one of the sources for RF pulses. Therefore, performing tactile measurements with currently existing tactile sensors, which include electrical wires, are impossible in many MIRS operations. Electrical wires included in the conventional sensors, such as piezoelectric sensors, usually induce eddy current fields which disturb the MRI images. In other words, in MRI environment, the use of electronics is not practical. Therefore, the surgical robot as well as its components such as sensors must be MRI compatible. Thus it is crucial to develop sensors performing tactile measurements even with the electromagnetic interference present in the surgical operating rooms. Hence, there is a need for novel concept of tactile sensor with components that are insensitive to electromagnetic fields. This ability allows sensors to work within environments with strong electromagnetic fields. In addition, for some specific types of surgeries, the sensor should be electrically passive due to the safety concerns of introducing electrical currents into the body. For instance, in intracardiac surgeries, to avoid disrupting normal electrical activities in the heart, which is an electrically active environment, the sensor must be electrically passive. As a result, the tactile sensor must be MRI compatible and electrically passive.

Accordingly, there is a need in the industry to provide an improved system for sensing a mechanical property of a sample. An object of the present invention is therefore to provide such a system.

SUMMARY OF THE INVENTION

In a broad aspect, the invention provides a sensing element for sensing a mechanical property of a sample defining a sample surface using a contact force exerted on the sensing element by the sample surface. The sensing element includes: a deformable element defining a deformable element first end and a substantially opposed deformable element second end, the deformable element defining a contact surface and a deformable section substantially in register with the contact surface between the deformable element first and second ends, the deformable section being deformable between an undeformed configuration and a deformed configuration, wherein the deformable section is in the undeformed configuration when no external forces are exerted on the contact surface and the deformable section is in the deformed configuration when the contact force is exerted on the contact surface; a deformation sensor operatively coupled to the deformable section for sensing and quantifying a deformation of the deformable section between the deformed and undeformed configurations, the deformation sensor being an optical deformation sensor; and a force sensor operatively coupled to the deformable element for sensing the contact forces exerted on the contact surface. When the contact and sample surfaces are abutted against each other and biased towards each other, the contact force is created on the contact surface and sensed by the force sensor; and the deformable section achieves the deformed configuration, the deformed configuration being sensed and quantified by the deformation sensor.

In a variant, the deformation sensor includes a deformation sensor interrupted optical waveguide defining a deformation sensor waveguide first segment, a deformation sensor waveguide second segment and a deformation sensor gap extending therebetween, the deformation sensor gap being provided substantially in register with the deformable section, the deformation sensor waveguide first and second segments being optically coupled to each other across the deformation sensor gap and secured to the deformable element with the deformation sensor waveguide first and second segments fixed with respect to the deformable section substantially adjacent the deformation sensor gap. Optical coupling between the deformation sensor waveguide first and second segments varies as the deformable section is moved between the undeformed and deformed configurations.

For the purpose of this document, an interrupted optical waveguide is an optical waveguide along which a section has been removed to create a gap. The light propagates without guidance across the gap. The reader skilled in the art will appreciate that in practice, the interrupted waveguide can be assembled using two waveguide segments that were not necessarily extending from each other prior to assembly of the sensing element. Also, the waveguide segments need not be of the same shape or made out of the same materials.

In some embodiments of the invention, the deformable element defines a waveguide receiving surface opposed to the contact surface, the deformation sensor interrupted optical waveguide being secured to the waveguide receiving surface.

In some embodiments of the invention, the deformation sensor interrupted optical waveguide is a deformation sensor optical fiber, the deformation sensor waveguide first and second segments being respectively a deformation sensor fiber first segment and a deformation sensor fiber second segment. For example, the waveguide receiving surface defines a substantially elongated fiber receiving groove extending thereinto, the deformation sensor fiber first and second segments being provided in the fiber receiving groove. In a specific example, the deformation sensor waveguide first and second segments are bonded to the deformable element in the fiber receiving groove.

In some embodiments of the invention, the deformation sensor waveguide first segment extends between the deformable element first end and the deformation sensor gap and the deformation sensor waveguide second segment extends between the deformable element second end and the deformation sensor gap.

In other embodiments of the invention, the deformation sensor waveguide first segment extends between the deformable element first end and the deformation sensor gap, and the deformation sensor waveguide second segment extends from the deformation sensor gap towards the deformable element second end and is provided with a light reflective end surface opposed to said deformation sensor gap.

In yet other embodiments of the invention, the deformable element defines an auxiliary light guiding element provided between the deformation sensor gap and the deformable element second end; the deformation sensor waveguide first segment extends between the deformable element first end and the deformation sensor gap; the deformation sensor waveguide second segment extends between the deformation sensor gap and the auxiliary light guiding element; the deformation sensor interrupted optical waveguide defines a deformation sensor waveguide third segment extending between the deformable element first end and the auxiliary light guiding element; and the auxiliary light guiding element optically couples the deformation sensor waveguide second and third segments. For example, the auxiliary light guiding element includes a mirror. In a specific example, the auxiliary light guiding element includes a pair of mirrors configured for changing a light direction propagation of light incoming at the mirrors by about 180 degrees. Also, for example, the deformation sensor waveguide second and third segments are in a substantially parallel and spaced apart relationship relative to each other.

In a variant, the sensing element further includes a base, the base and the deformable element extending in a substantially parallel and spaced apart relationship relative to each other. In some embodiments of the invention, a first spacing element extends between the base and the deformable element substantially adjacent the deformable element first end. For example, the deformable element second end is movable with respect to the base. In another example, a second spacing element extends between the base and the deformable element substantially adjacent the deformable element second end.

In some embodiments of the invention, in the undeformed configuration, the deformation sensor waveguide first and second segments have substantially coaxial optical axes.

In a variant, the deformation sensor includes at least two deformation sensor interrupted optical waveguides each defining a respective deformation sensor waveguide first segment, a respective deformation sensor waveguide second segment and a respective deformation sensor gap extending therebetween, the deformation sensor gaps being provided substantially in register with the deformable section, the respective deformation sensor waveguide first and second segments being optically coupled to each other across the respective deformation sensor gaps and each secured to the deformable element with the deformation sensor waveguide first and second segments fixed with respect to the deformable section substantially adjacent the deformation sensor gaps. Optical coupling between the deformation sensor waveguide first and second segments varies as the deformable section is moved between the undeformed and deformed configurations.

In some embodiments of the invention, the deformation sensor interrupted optical waveguides extend substantially parallel to each other in a laterally spaced apart relationship relatively to each other.

In some embodiments of the invention, the deformation sensor gaps are longitudinally offset with respect to each other.

In a variant, the sensing element includes a base, the base and the deformable element extending in a spaced apart relationship relative to each other; and a first spacing element extending between the base and the deformable element. For example, the base and the deformable element extend in a substantially parallel relationship relative to each other.

In a variant, the force sensor is an optical force sensor. In some embodiments of the invention, the force sensor includes a force sensor interrupted optical waveguide defining a force sensor waveguide first segment, a force sensor waveguide second segment and a force sensor gap extending therebetween, the force sensor waveguide first segment extending through the first spacing element and being fixed relative thereto substantially adjacent the force sensor gap, the force sensor waveguide second segment being supported by the base and fixed relative thereto substantially adjacent the force sensor gap, the force sensor waveguide first and second segments being optically coupled to each other across the force sensor gap, the first spacing element including a first support resiliently deformable section provided between the base and the force sensor optical waveguide first segment. When the first support resiliently deformable section is compressed, the force sensor waveguide first segment is moved relative to the force sensor waveguide second segment, which changes optical coupling between the force sensor waveguide first and second segments. For example, the first support resiliently deformable section is made out of a material selected from the group consisting of Polydimethylsiloxane (PDMS), silicone rubbers, epoxy, and rubbers.

In some embodiments of the invention, the force sensor interrupted optical waveguide is a force sensor optical fiber, the force sensor waveguide first and second segments being respectively a force sensor fiber first segment and a force sensor fiber second segment. For example, the force sensor fiber first and second segments are inserted respectively through a first ferrule and a second ferrule, the first ferrule extending through the first spacing element and the second ferrule being supported by the base. Also for example, the first spacing element is substantially adjacent the deformable element first end.

In some embodiments of the invention, a second spacing element extends between the base and the deformable element, the first and second spacing elements being spaced apart from each other and respectively provided substantially adjacent the deformable element first and second ends. For example, in these embodiments, the force sensor includes a force sensor first interrupted optical waveguide defining a force sensor first waveguide first segment, a force sensor first waveguide second segment and a force sensor first gap extending therebetween, the force sensor first waveguide first segment extending through the first spacing element and being fixed relative thereto substantially adjacent the force sensor first gap, the force sensor first waveguide second segment being supported by the base and fixed relative thereto substantially adjacent the force sensor first gap, the force sensor first waveguide first and second segments being optically coupled to each other across the force sensor first gap, the first spacing element including a first support resiliently deformable section provided between the base and the force sensor first waveguide first segment; a force sensor second interrupted optical waveguide defining a force sensor second waveguide first segment, a force sensor second waveguide second segment and a force sensor second gap extending therebetween, the force sensor second waveguide first segment extending through the second spacing element and being fixed relative thereto substantially adjacent the force sensor second gap, the force sensor second waveguide second segment being supported by the base and fixed relative thereto substantially adjacent the force sensor second gap, the force sensor second waveguide first and second segments being optically coupled to each other across the force sensor second gap, the second spacing element including a second support resiliently deformable section provided between the base and the force sensor second waveguide first segment. When the first support resiliently deformable section is compressed, the force sensor first waveguide first segment is moved relative to the force sensor first waveguide second segment, which changes optical coupling between the force sensor first waveguide first and second segments, and when the second support resiliently deformable section is compressed, the force sensor second waveguide first segment is moved relative to the force sensor second waveguide second segment, which changes optical coupling between the force sensor second waveguide first and second segments.

In a variant, the force sensor includes a piezoresistive element provided between the first spacing element and the base.

In another broad aspect, the invention provides a system for measuring a mechanical property of a sample defining a sample surface using a contact force exerted by the sample surface. The system includes a sensing element as recited above; a light source optically coupled to the deformation sensor waveguide first segment opposed to the deformation sensor gap for emitting a source light in the deformation sensor waveguide first segment; a light detector optically coupled to the deformation sensor waveguide second segment opposed to the deformation sensor gap for detecting an intensity of light received from the deformation sensor waveguide second segment; a controller operatively coupled to the light detector for receiving the intensity of light received from the deformation sensor waveguide second segment when the source light is emitted in the deformation sensor waveguide first segment and computing a deformation of the deformable section using a power loss of the source light across the sensing element; and an output element for outputting the deformation.

In yet another broad aspect, the invention provides a system for measuring a mechanical property of a sample defining a sample surface using a contact force exerted by the sample surface. The system includes a sensing element as recited above; a light source optically coupled to the force sensor waveguide first segment opposed to the force sensor gap for emitting a source light in the force sensor waveguide first segment; a light detector optically coupled to the force sensor waveguide second segment opposed to the force sensor gap for detecting an intensity of light received from the force sensor waveguide second segment; a controller operatively coupled to the light detector for receiving the intensity of light received from the force sensor waveguide second segment when the source light is emitted in the force sensor waveguide first segment and computing the contact force exerted on the contact surface using a power loss of the source light across the sensing element; and an output element for outputting the contact force.

In yet another broad aspect, the invention provides a deformation detector for detecting a deformation of a deformable element, the deformation detector including: a deformation sensor interrupted optical waveguide defining a deformation sensor waveguide first segment, a deformation sensor waveguide second segment and a deformation sensor gap extending therebetween, the deformation sensor waveguide first and second segments being secured to the deformable element with the deformation sensor waveguide first and second segments fixed with respect to the deformable element adjacent the deformation sensor gap; a light source optically coupled to the deformation sensor waveguide first segment opposed to the deformation sensor gap for emitting a source light in the deformation sensor waveguide first segment; a light detector optically coupled to the deformation sensor waveguide second segment opposed to the deformation sensor gap for detecting an intensity of light received from the deformation sensor waveguide second segment; a controller operatively coupled to the light detector for receiving the intensity of light received from the deformation sensor waveguide second segment when the source light is emitted in the deformation sensor waveguide first segment and computing a deformation of the deformable element using a power loss of the source light across the sensing element; and an output element for outputting the deformation.

In yet another broad aspect, the invention provides a force detector for detecting a force, the force detector comprising: a contact element defining a contact surface for exerting the force thereagainst; a base; a spacing element extending between the base and the contact element; a force sensor interrupted optical waveguide defining a force sensor waveguide first segment, a force sensor waveguide second segment and a force sensor gap extending therebetween, the force sensor waveguide first segment extending through the spacing element, the force sensor waveguide second segment being supported by the base, the spacing element including a support resiliently deformable section provided between the base and the force sensor optical waveguide first segment; a light source optically coupled to the force sensor waveguide first segment opposed to the force sensor gap for emitting a source light in the force sensor waveguide first segment; a light detector optically coupled to the force sensor waveguide second segment opposed to the force sensor gap for detecting an intensity of light received from the force sensor waveguide second segment; a controller operatively coupled to the light detector for receiving the intensity of light received from the force sensor waveguide second segment when the source light is emitted in the force sensor waveguide first segment and computing the contact force exerted on the contact surface using a power loss of the source light across the sensing element; and an output element for outputting the contact force.

Advantageously, in some embodiments of the invention, the proposed sensing element is both MRI compatible and electrically passive. In some embodiments of the invention, the proposed sensor measures the biasing force, the position of the biasing force along the deformable section, and the softness/hardness of contact objects in both static and dynamic loading conditions while being MRI-compatible and electrically passive. In addition, it performs the measurements by having only one single moving part.

Although the present patent application often makes reference to applications in the field of robotic surgery, the devices and methods of the present application also have many other applications. For example, force and softness sensing systems are usable in many hostile environmental conditions, such as, for example, in space exploration. Indeed, tactile feedback is of paramount importance in the performance of many tasks, but protective gear often reduces such feedback. Also, in very hostile environments, robotic systems are used, which could also benefit greatly from the present invention. Furthermore, the proposed system can measure other properties of samples, such as hyperelastic properties, viscoelastic properties, local discontinuities in the mechanical properties of the sample such as the degree of softness/hardness, among other possibilities.

Other objects, advantages and features of the present invention will become more apparent upon reading of the following non-restrictive description of preferred embodiments thereof, given by way of example only and in relation with the following Figures.

BRIEF DESCRIPTION OF THE DRAWINGS

FIG. 6, in front elevation view, illustrates a deformable element and a deformation sensor both part of the sensing element shown in FIGS. 2 to 5;

FIG. 7, in bottom plan view, illustrates the deformable element and deformation sensor shown in FIG. 6;

FIG. 8, in bottom plan view, illustrates an alternative deformable element and deformation sensor usable in the softness sensor shown in FIGS. 2 to 5;

FIG. 9, in a partial perspective view, illustrates the alternative deformable element shown in FIG. 8;

DETAILED DESCRIPTION

Figure 1:
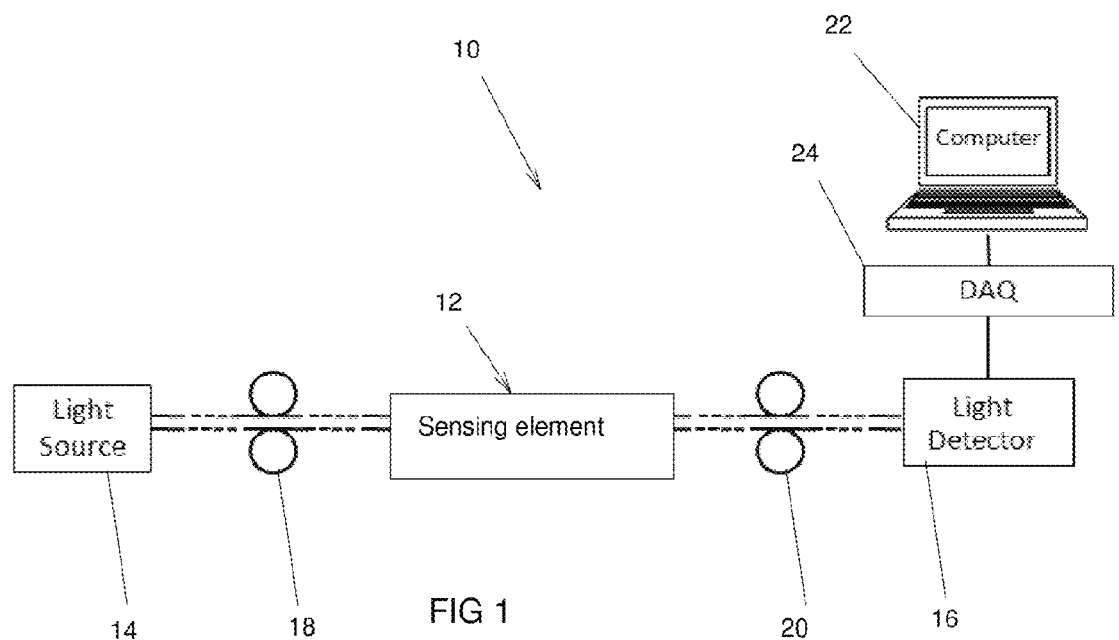
FIG. 1, in a schematic view, illustrates a system for sensing a mechanical property of a sample in accordance with an embodiment of the present invention, the system including a sensing element.
Figure 15A:
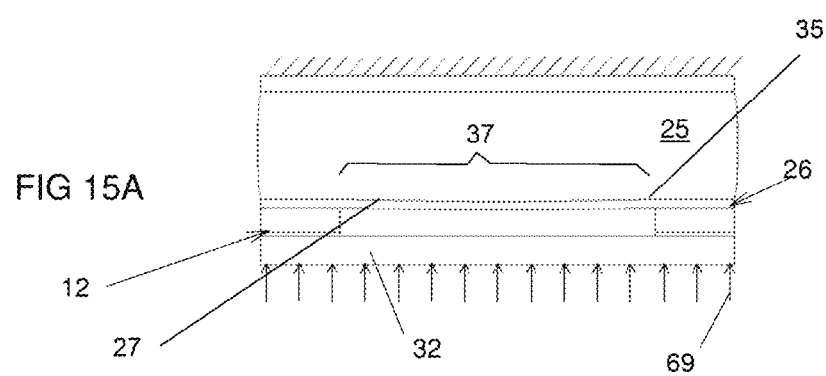
FIGS. 15A and 15B illustrate a deformation of the deformable element shown in FIG. 7 as a function of an increasing softness of a sample when the deformation sensor shown in FIGS. 2 to 5 is biased against the object.
Figure 15B:
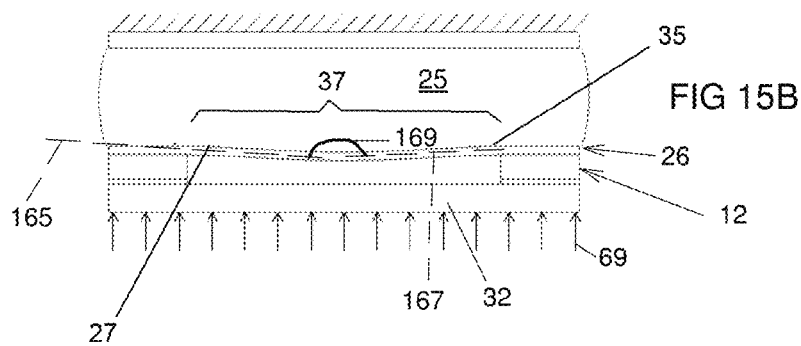

Referring to FIG. 1, there is shown a system 10 for measuring a mechanical property of a sample 25, shown in FIGS. 15A and 15B, defining a sample surface 27 using a contact force exerted by the sample surface 27. Examples of measurable mechanical properties include variations in force distributions, softness/hardness, hyperelastic properties, viscoelastic properties, and local discontinuities in the mechanical properties of the sample such as the degree of softness/hardness, among other possibilities.

Returning to FIG. 1, the system 10 includes a sensing element 12. The system also includes a light source 14 and a light detector 16. Light emitted by the light source 14 is transmitted to the sensing element 12 through input optical fibres generally designated by the reference numeral 18. The sensing element 12 transmits partially or totally light received by the input optical fibres 18 according to the value of the measured mechanical property of the sample 25. The resulting light is transmitted to the light detector 16 through output optical fibres generally designated by reference numeral 20. The light detector 16 detects the intensity of light incoming from the output optical fibres 20 and transmits this information to a computer 22 that includes a proper interface 24 for interfacing with the light detector 16. After suitable processing, the resulting mechanical property information is either displayed on the computer 22 in a conventional manner, or transmitted from the computer 22 to a suitable alternative display, not shown in the drawings. The computer 22 is therefore a controller operatively coupled to the light detector 16 for receiving the intensity of light received from the sensing element 12 when the source light is emitted in the input optical fibres 18 and computing the mechanical property using a power loss of the source light across the sensing element 12. The computer 22 also includes an output element for outputting the mechanical property, such as a display, a storage medium or a network interface, among other possibilities.

The sensing element 12 can be provided on a grasper (not shown in the drawings), or, in alternative embodiments of the invention, can be integrated at the tip of a catheter (not shown in the drawings). In yet other embodiments of the invention, the sensing element 12 is integrated to any suitable device allowing positioning of the sensing element 12 at the location at which the mechanical property is to be measured. Also, in alternative embodiments of the invention, more than one sensing elements 12 are integrated to the device allowing positioning of the sensing elements 12.

The sensing element 12 is used for sensing the mechanical property of the sample 25, as seen for example in FIG. 15A, by abutting the sensing element 12 against the sample 25 and biasing the sensing element 12 toward the sample 25 with a biasing force 69. In the remainder of this document, the degree of softness of the sample 25 is used as an example of a mechanical property that can be measured by the system 10. However, this choice is for illustrative purpose and other mechanical properties, such as those mentioned hereinabove, are measurable without departing from the scope of the invention.

Figure 2:
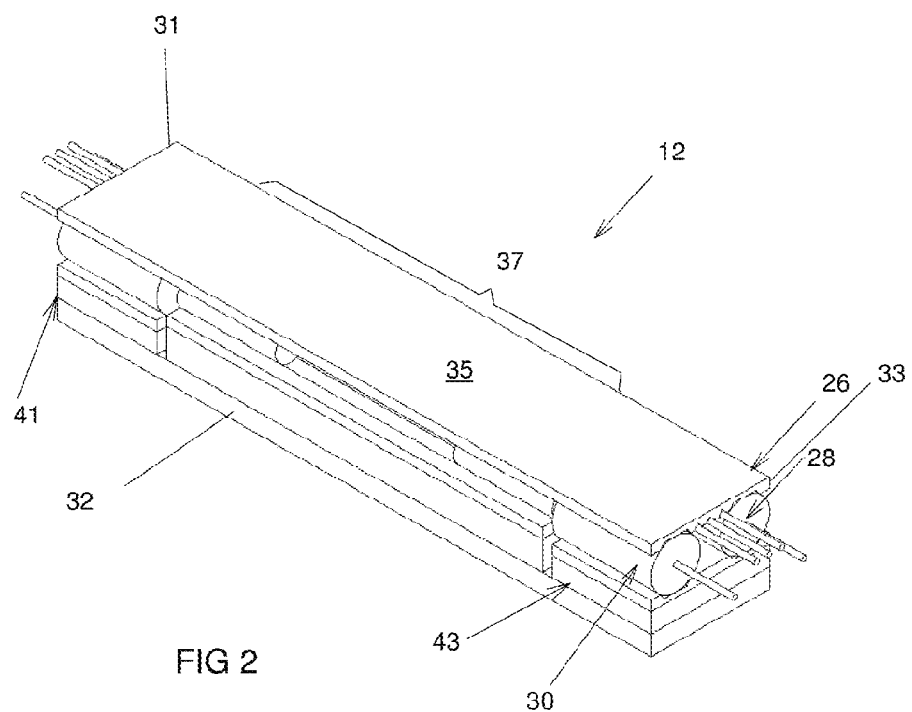
FIG. 2, in a perspective view, illustrates the sensing element part of the system shown in FIG. 1.

Referring to FIG. 2, the sensing element 12 includes a deformable element 26 defining a deformable element first end 31 and a substantially opposed deformable element second end 33, the deformable element 26 defining a contact surface 35 and a deformable section 37 substantially in register with the contact surface between the deformable element first and second ends 31 and 33. The deformable section 37 is deformable between an undeformed configuration, shown for example in FIG. 2, and a deformed configuration, shown for example in FIG. 15A. The deformable section 37 is in the undeformed configuration when no external forces are exerted on the contact surface 35 and the deformable section 37 is in the deformed configuration when the contact force is exerted on the contact surface 35 by the sample 25.

Returning to FIG. 2, a deformation sensor 28 is operatively coupled to the deformable section 37 for sensing and quantifying a deformation of the deformable section 37 between the deformed and undeformed configurations. The deformation sensor 28 is an optical deformation sensor that uses changes in a parameter of light that is propagated in the deformation sensor 28 as a function of the deformation of the deformable section 37 to sense and quantify the deformation of the deformable section 37. For example, in the embodiment shown in the drawings, the parameter is the power of the light, but other parameters such as phase and polarization, among other possibilities, are changed in alternative embodiments of the invention. A force sensor 30 is operatively coupled to the deformable section 37 for sensing the contact force exerted onto the contact surface 35 by the sample 25 when the deformable section 37 is biased toward the sample 25 with a biasing force.

When the contact and sample surfaces 35 and 27 are abutted against each other and biased toward each other, the contact force is created on the contact surface 35 and sensed by the force sensor 30 and the deformable section 37 achieves the deformed configuration, the deformed configuration being sensed and quantified by the deformation sensor 28.

Figure 3:
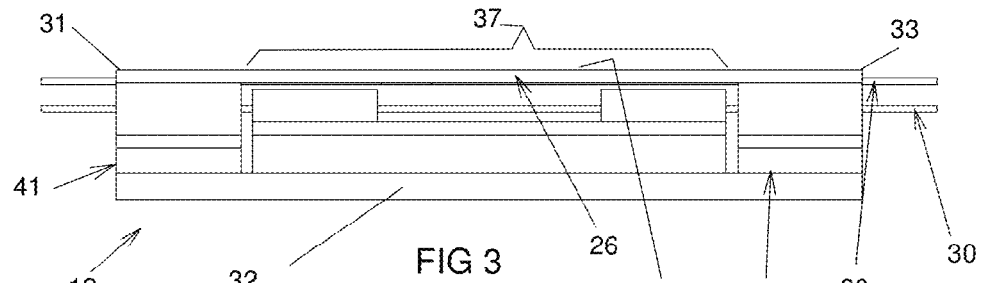
FIG. 3, in a side elevation view, illustrates the sensing element shown in FIG. 2.

Typically, the sensing element 12 includes a base 32 for supporting the deformable element 26, the deformation sensor 28 and the force sensor 30. As better seen in FIG. 3, the deformable element 26 is mechanically coupled to the base 32 and supported in a spaced apart relationship relatively thereto in a manner such that the deformable section 37 is deformable with respect to the base 32. Typically, but not necessarily, the base 32 and the deformable element 26 extend in a substantially parallel relationship relative to each other.

Typically, the sensing element 12 is substantially elongated and the deformable element 26 is supported substantially adjacent at two substantially longitudinally opposed ends thereof so as to allow deformation of its midsection when a force is exerted thereonto. To that effect, a first spacing element 41 extends between the base 32 and the deformable element 26. Typically, the first spacing element 41 extends between the base 32 and the deformable element 26 substantially adjacent the deformable element first end 31. In some embodiments of the invention, a second spacing element 41 extends between the base 32 and the deformable element 26, typically substantially adjacent the deformable element second end 33. The first and second spacing elements 41 and 43 link and mechanically couple the base 32 and the deformable element 26 to each other. However, in alternative embodiments of the invention (not shown in the drawings), the second spacing element 43 is omitted and the deformable element second end 33 is movable with respect to the base 32. In other words, the deformable element 26 is then supported in a cantilevered configuration. In yet other embodiments of the invention, the base 32 and the deformable element 26 are coupled to each other in any suitable manner. Also, sensing elements 12 in which more than one deformable elements 26 are present are also within the scope of the present invention.

Figure 4:
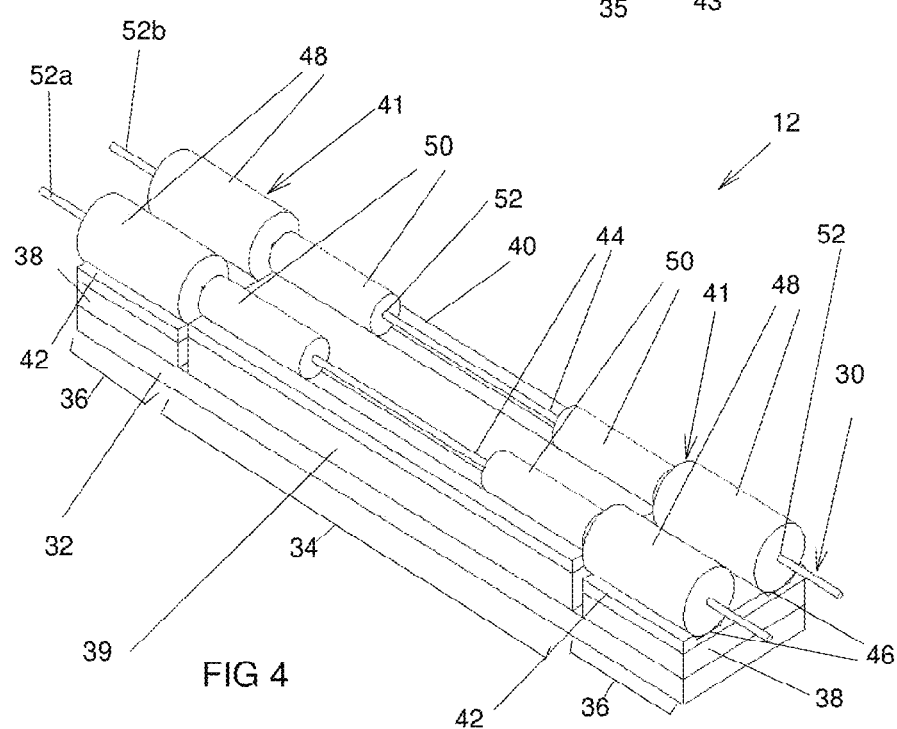
FIG. 4, in a perspective view with parts removed, illustrates the sensing element shown in FIGS. 2 and 3.
Figure 5:
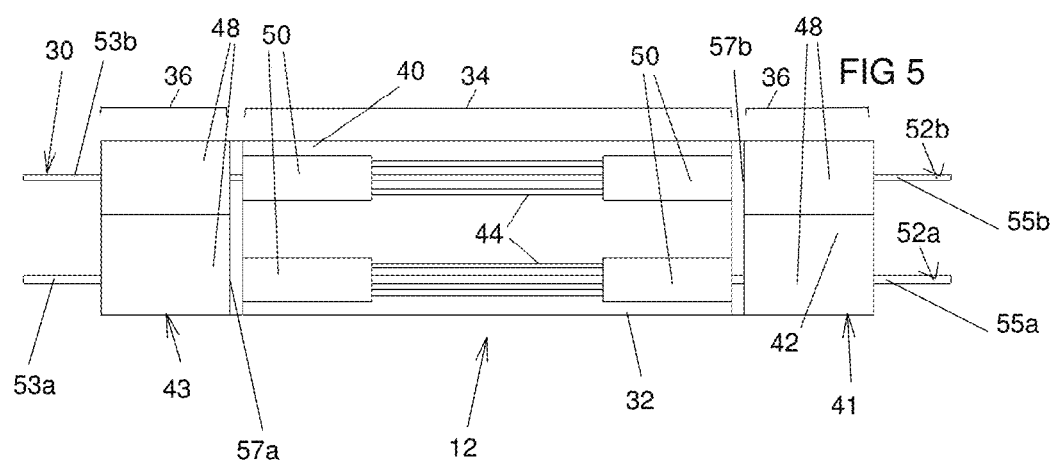
FIG. 5, in a top plan view with parts removed, illustrates the sensing element shown in FIGS. 2 to 4.

FIGS. 4 and 5 better illustrate the force sensor 30. The force sensor 30 shown in FIGS. 4 and 5 is configured for sensing forces at opposed ends of the sensing element 12. However, other configurations are within the scope of the present invention. For example, a force sensor could be configured to sense force at only one end of the sensing element 12. The force sensor 30 is an optical force sensor that uses changes in a parameter of light that is propagated in the force sensor 30 as a function of the contact force exerted of the deformable element 26 to sense and quantify the contact force exerted on the deformable element 26.

The force sensor 30 includes a stationary segment 34 and a pair of mobile segments 36 that are substantially longitudinally opposed with respect to each other. The stationary segment 34 is provided between the mobile segments 36. The mobile segments 36 and the stationary segment 34 all extend from the base 32 substantially toward the deformable element 26. The stationary segment 34 is decoupled from the deformable element 26 such that when the deformable section 37 deforms due to a contact force exerted thereonto, no force is exerted on the stationary segment 34 toward the base 32. The mobile segments 36 are, in opposition, operatively coupled to the deformable element 26 so as to receive forces exerted on the deformable section 37. Each mobile segment 36 is part of a respective one of the first and second spacing elements 41 and 43. Therefore, the mobile segments 36 extend between the base 32 and the deformable element 26 at substantially longitudinally spaced apart locations along the sensing element 12.

The first and second spacing elements 41 and 43 each include a compressible element 38, which defines a spacing element resiliently deformable element, a mobile optical element support 42 and a pair of ferrules 48. The compressible element 38 is provided between the base 32 and the deformable element 26 so as to be compressed when a force is exerted onto the deformable element 26. The compressible element 38 is typically much more compressible than either the base 32 or the deformable element 26. Selection of the compressibility of the compressible element 38 allows for adjusting the range of forces can be sensed precisely and effectively by the force sensor 30. In the embodiment of the invention shown in the drawings, the compressible elements 38 each extend directly from the base 32 toward the deformable element 26. It should be noted that in some embodiments of the invention, for ease of manufacturing reasons, the stationary segments 34 also includes a compressible element 39 extending from the base 32 that is made out of the same material used to make the compressible elements 38. However, since no forces are transmitted to this compressible element 39 in operation, the stationary segment 34 remains unaffected by the forces exerted onto the deformable element 26. To achieve this result, the compressible element 39 is longitudinally spaced apart from the compressible elements 38. The compressible elements 38 are made out of any suitable material, such as Polydimethylsiloxane (PDMS), a silicone rubber, an epoxy, a rubber, or any other suitable material.

The stationary segment 34 includes a stationary optical element support 40. Similarly, the first and second spacing elements 41 and 43 each include one of the mobile optical element supports 42. The stationary and mobile optical element supports 40 and 42 are made out of material that is typically much less compressible than the one making up the compressible elements 38 and 39. The stationary and mobile optical element supports 40 and 42 are provided between the compressible elements 38 and 39 and the deformable element 26. The stationary and mobile optical element supports 40 and 42 define each a pair of substantially longitudinally extending support grooves 44 and 46. In each of the stationary and mobile optical element supports 40 and 42, the support grooves 44 and 46 are substantially parallel to each other and extend along the whole length of the stationary and mobile optical element supports 40 and 42, inwardly toward the base 32. The stationary and mobile optical element supports 40 and 42 are usable for supporting optical components that will detect movements of the stationary and mobile optical element supports 40 and 42 as forces are exerted onto the deformable element 26. The support grooves 44 and 46, and all the other grooves described in this document, are manufactured using any suitable technique, such as, for example, microelectromechanical system (MEMS) anisotropic etching.

One of the ferrules 48 is inserted in each of the support grooves 46 of the mobile optical element supports 42. A pair of substantially longitudinally spaced apart ferrules 50 is inserted in each of the support grooves 44 of the stationary optical element support 40. Each of the ferrules 48 and 50 is substantially cylindrical and defines a passageway 52 extending substantially longitudinally therethrough. The ferrules 48 inserted in the support grooves 46 of the mobile optical element supports 42 are substantially similarly dimensioned. Similarly, the ferrules 50 inserted in the support grooves 44 of the stationary optical element support 40 are substantially similarly dimensioned. The ferrules 48 and 50 are dimensioned such that when the deformable element 26 is positioned above the ferrules 48 and 50, the deformable element 26 abuts against the ferrules 48, but does not contact the ferrules 50, even when the deformable section 37 is in the deformed configuration. Also, the ferrules 48 and 50 are dimensioned so as to be laterally fixed relatively to the support grooves 46 and 44. Longitudinal immobilization is either provided through friction, or by fixing with a glue, or by suitable optical fibre bonding techniques among other possibilities. Each of the ferrules 48 is substantially axially aligned with and substantially adjacent to a corresponding ferrule 50. When no force is exerted onto the deformable element 26 and the base 32, the passageways 52 of substantially adjacent ferrules 48 and 50 are substantially axially aligned.

A first force sensor optical fibre 52a extends through all the passageways 52 of two substantially axially aligned ferrules 48 and their adjacent ferrules 50. A second force sensor optical fibre 52b extends through all the passageways 52 of the other two substantially axially aligned ferrules 48 and their adjacent ferrules 50. The first and second force sensing optical fibres 52a and 52b are secured inside the ferrules 48 and 50 in a conventional manner. Therefore, two optical paths extending substantially longitudinally along the sensing element 12 are formed. The two optical paths are substantially parallel to each other. Each of the first and second force sensing optical fibres 52a and 52b is interrupted between a respective one of the mobile segments 36 and the stationary segment 34, as better seen in FIG. 5. Each of the first and second force sensing optical fibres 52a and 52b are optically coupled respectively to one of the input optical fibres 18 at one end thereof and to one of the output optical fibres 20 at the other end thereof. The force sensing optical fibres 52a and 52b, and all the other optical fibres described in this document can be single mode or multimode.

Referring more specifically to FIG. 5, the first force sensing optical fibre 52a therefore includes a force sensor first fibre first segment 53a, a force sensor first fibre second segment 55a and a force sensor first gap 57a extending therebetween. The force sensor first gap 57a is located between the first spacing element 41 and the stationary segment 34. The force sensor first fibre first and second segments 53a and 55a are optically coupled to each other across the force sensor first gap 57a. Similarly, the second force sensing optical fibre 52b includes a force sensor second fibre first segment 53b, a force sensor second fibre second segment 55b and a force sensor second gap 57b extending therebetween. The force sensor second gap 57b is located between the second spacing element 43 and the stationary segment 34. The force sensor second fibre first and second segments 53b and 55b are optically coupled to each other across the force sensor first gap 57b.

The force sensor first fibre first segment 53a and the force sensor second fibre second segment 55b therefore extend respectively through the first and second spacing elements 41 and 43 and are fixed relative thereto substantially adjacent the respective force sensor first and second gaps 57a and 57b. The force sensor second fibre first segment 53b and the force sensor first fibre second segment 55a are supported by the base 32 and fixed relative thereto substantially adjacent respectively the force sensor first and second gaps 57a and 57b.

In alternative embodiments of the invention, the above-mentioned optical fibres can be replaced by other types of optical waveguides that define similar segments, such as waveguides made of Silicon, Silica, Silicon-On-Insulator (SOI), InP, GaAs, Polydimethylsiloxane (PDMS), Poly(methyl methacrylate) (PMMA), other polymer platforms and optically transmitting materials in their respective wavelength ranges, or a combination of the above materials, among others, implemented for waveguides. Also, the optical fibres are any suitable type of optical fibre, such as single-mode or multi-mode fibres, glass fibres, plastic fibres, among other possibilities. Also, in alternative embodiments of the invention, the optical waveguides are not mounted using the ferrules 48 and 50, but are otherwise attached to the remainder of the sensing element 12 using other methods known in the art.

FIGS. 6 and 7 illustrate the deformable element 26. In addition to the contact surface 35, the deformable section 37 typically defines a waveguide receiving surface 54 opposed to the contact surface 35 for receiving one or more optical waveguides, as detailed hereinbelow. However, in alternative embodiments of the invention, the optical waveguides are coupled to the deformable element 26 in any other suitable manner, for example by being embedded therein. The waveguide receiving surface 54 faces toward the base 32 and the contact surface 35 faces toward the sample 25 for which the mechanical property is to be assessed.

The waveguide receiving surface 54 is provided with substantially longitudinally extending support grooves 58 each positioned, configured and sized for substantially fittingly receiving thereinto a portion of a pair of substantially axially aligned ferrules 48. The ferrules 48 are therefore provided between the deformable element 26 and the mobile optical element supports 42 and transmit forces exerted on the deformable element 26 to the compressible elements 38.

The waveguide receiving surface 54 is also provided with substantially parallel and laterally spaced apart fibre receiving grooves 60. The fibre receiving grooves 60 each extend substantially longitudinally along the whole length of the deformable element 26. Typically, the fibre receiving grooves 60 have a substantially V-shaped transversal cross-sectional configuration, but other configurations, such as square or circular configurations, among other possibilities, are within the scope of the invention. V-shaped cross-sections can be micro-machined, for example by wet anisotropic silicon etching techniques. Also, in alternative embodiments of the invention, the fibre receiving grooves 60 have any other suitable configuration.

The deformable element 26 has any suitable shape, such as an elongated shape, as in the drawings, but also a substantially square shape and is made of any suitable material, such as silicon, a metal or a polymer and combinations thereof, among other possibilities.

A deformation sensor optical fibre 62 is inserted in and along each of the fibre receiving grooves 60 and is secured thereto. While three deformation sensor optical fibres 62 are shown in the drawings, any suitable number of deformation sensor optical fibres 62 can be provided, as long as a corresponding number of fibre receiving grooves 60 is provided. By using at least three deformation sensor optical fibres 62 in the shown configuration, the position of a concentrated force can be measured precisely.

Each of the deformation sensor optical fibres 62 is interrupted by a respective deformation sensor gap 64, better seen in FIG. 7, provided substantially in register with the deformable section 37. Therefore, each deformation sensor optical fibre 62 is split into a deformation sensor fibre first segment 65 and a deformation sensor fibre second segment 67 with the deformation sensor gap 64 extending therebetween. Each of the deformation sensor fibre first segments 65 extends between the deformable element first end 31 and the deformation sensor gap 64 of the deformation sensor optical fibre 62 to which it belongs and each of the deformation sensor fibre second segments 67 extends between the deformable element second end 33 and the deformation sensor gap 64 of the deformation sensor optical fibre 62 to which it belongs.

The deformation sensor fibre first and second segments 65 and 67 are optically coupled to each other across the deformation sensor gap 64 and secured to the deformable element 26 with the deformation sensor fibre first and second segments 65 and 67 fixed with respect to the deformable section 37 substantially adjacent the deformation sensor gap 64. In some embodiments of the invention, the deformation sensor gaps 64 are located at different longitudinal positions along the deformable section 37, which allows deformation measurements to be taken at different longitudinal locations along the deformable section 37. In some embodiments of the invention, in the undeformed configuration, the deformation sensor fibre first and second segments 65 and 67 have substantially coaxial optical axes.

Each of the deformation sensor optical fibres 62 is optically coupled to one of the input optical fibres 18 at one end thereof and to one of the output optical fibres 20 at the other end thereof. The deformation sensor optical fibres 62 are secured inside the fibre receiving grooves 60 in a conventional manner, for example using a glue or optical fibre bonding techniques. Typically, but not exclusively, the fibre receiving grooves 60 are provided laterally inwardly with respect to the support grooves 58. Also, similarly to the force sensor optical fibres 52a and 52b, in alternative embodiments of the invention, the deformation sensor optical fibres 62 are replaced by any other suitable optical waveguide, such as those mentioned hereinabove in the context of the force sensor optical fibres 52a and 52b.

In use, the sensing element 12 works as follows. Generally speaking, optical coupling between the deformation sensor fibre first and second segments 65 and 67 varies as the deformable section 37 is moved between the undeformed and deformed configurations. Measurements of this optical coupling allows determination of the deformation of the deformable section 37. Also, when the compressible elements 38 are compressed, the force sensor fibre first segments 53a and 53b are moved relative to the force sensor fibre second segments 55a and 55b, which changes optical coupling between the force sensor waveguide first and second segments 53a, 53b and 55a, 55b. Measurements of this optical coupling allows determination of the magnitude of the contact force exerted on the deformable section 37.

In greater details, the sensing element 12 is used as follows, here illustrated in the context of softness/hardness measurements. First, as seen for example in FIG. 15A, the sensing element 12 is positioned against the sample 25 and a biasing force 69 is exerted toward the sample 25, for example by exerting a substantially uniformly distributed biasing force 69 on the base 32 toward the sample 25. This biasing force 69, which produces a contact force exerted by the sample 25 on the contact surface 35 by Newton's third law, has two effects on the sensing elements 12.

The first effect is to compress the compressible elements 38. This compression changes the alignments between the passageways 52 of the ferrules 48 and 50 across the force sensor gaps 57a and 57b. In turn, this changes the transmittance of light emitted by the light source 14 through the first and second force sensing optical fibres 52a and 52b. This reduction in transmittance is detected at the light detector 16. The computer 22 can then use the measured transmittance to assess the force exerted onto the sensing element 12. Since two compressible elements 38 are provided, an average force and its longitudinal gradient can be assessed. These forces are assessed either by calibrating the sensing element 12, or by theoretical calculations based on the mechanical properties of the various components of the sensing element 12.

The second effect is to deform the deformable section 37 as the deformable element 26 is pushed into the sample 25. This deformation changes the alignment between segments of the deformation sensor optical fibres 62 positioned across the deformation sensor gaps 64. Such changes in alignment may be angular, as in the present embodiment, or in translation, similar to the case of the force sensing, as described above. Any change in alignment from a direct coaxial alignment in the deformation sensor optical fibres 62 (ie translation or angular movements) across the deformation sensor gaps 64 results in changes in light transmission across the deformation sensor gaps 64, which are used to quantify deformation of the deformable section 37, thus providing a deformation sensor.

Indeed, as mentioned hereinabove, the deformation sensor fibre first and second segments 65 and 67 are optically coupled to each other across the deformation sensor gap 64 and secured to the deformable element 26 with the deformation sensor fibre first and second segments 65 and 67 fixed with respect to the deformable section 37 substantially adjacent the deformation sensor gap 64. As the deformable section 37 is deformed, alignment between the deformation sensor fibre first and second segments 65 and 67 will be changed across the gap 64. Notably, as seen in FIG. 15B for example, this deformation, for example bending of the deformable section 37, will change the angle 169 between the longitudinal axes 165 and 167 of the deformation sensor fibre first and second segments 65 and 67 (not seen in FIG. 15B), which in turn will influence the quantity of light that is transmitted between the deformation sensor fibre first and second segments 65 and 67. The angle 169 is 180 degrees before any deformation, and is reduced with deformation of the deformable element 26. In turn, this reduces the transmittance of light emitted by the light source 14 through the deformation sensor optical fibres 62 as the longitudinal axes 165 and 167 the deformation sensor fibre first and second segments 65 and 67 are then no longer collinear. This reduction in transmittance is detected at the light detector 16. The computer 22 can then use the measured transmittance to assess the deformation of the deformable section 37. Since many deformation sensor gaps 64 are provided along the length of the deformable section 37, non-uniform deformations of the deformable section 37 are detectable.

Figure 16:
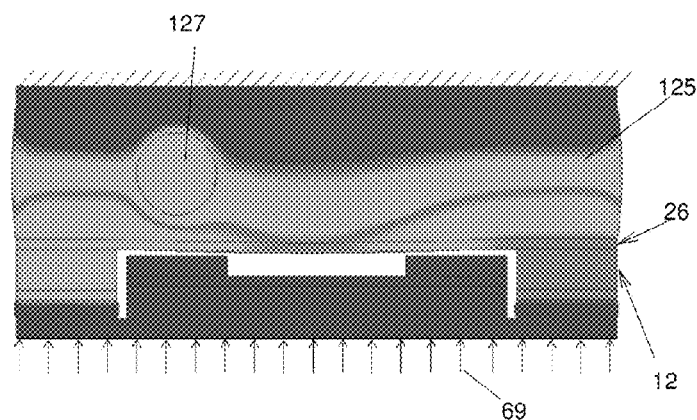
FIG. 16, in a front cross-sectional view, illustrates a simulation of the sensing element shown in FIGS. 2 to 5 abutting against a sample that includes a hard inclusion.

As shown in comparing FIGS. 15A and 15B, compared to a hard sample 25, softer sample 25 result in a greater deformation of the deformable section 37 for a given same applied force 69. Also, if the sample 25 is not uniform in mechanical properties, as seen for example in FIG. 16 in which an alternative sample 125 includes a hard inclusion 127, the force detected at both ends of the sensing element 12 will not necessarily be the same. The grey scale in this Figure indicates the deformation in the sample 125 when the force 69 is exerted on the sensing element 12. In addition, the deformation of the deformable section 37 will not be longitudinally uniform. By using finite element modelling, or any other suitable method, it is possible to compute an approximation of the softness/hardness distribution in the sample 125.

FIGS. 8 and 9 illustrate an alternative deformable element 126 and an alternative deformation sensor 128 both usable instead of the deformable element 26 and deformation sensor 28 in the sensing element 12. The deformable element 126 defines alternative fibre receiving grooves 160. Instead of being substantially elongated and axially open at both ends of the deformable element 126, the alternative fibre receiving grooves 160 are each substantially U-shaped in the plane of the deformable element 126 and open only at one end thereof. More specifically, each of the fibre receiving grooves 160 defines a pair of substantially rectilinear sections 161 (better seen in FIG. 9) provided in a substantially adjacent and substantially parallel relationship with respect to each other. The rectilinear sections 161 are axially open at one end 163 thereof, as seen in FIG. 8, and are linked to each other at the other end 165 thereof by a linking section 167. Each of the linking sections 167 defines an auxiliary light guiding element provided between the deformation sensor gaps 164 and the deformable element second end 33. To that effect, the linking section 167 includes a pair of optically reflective surfaces 171, or mirrors, better seen in FIG. 9, so that light incoming axially through one of the rectilinear sections 161 is reflected back into the other rectilinear sections 161 of the same fibre receiving groove 160. In other words, the optically reflective surfaces 171 are configured for changing a light direction propagation of light incoming at the optically reflective surfaces 171 by about 180 degrees.

Deformation sensor optical fibres 162a and 162b are provided in a respective one of the rectilinear sections 161 of each fibre receiving groove 160. The deformation sensor optical fibres 162a are continuous and uninterrupted. The deformation sensor optical fibres 162b each define a deformation sensor gap 164 therealong. The deformation sensor gaps 164 are provided at different longitudinal locations along the deformable section 137.

In use, light from the input optical fibres 18 is provided to the deformation sensor optical fibres 162a to propagate therethrough to the linking section 167, at which point it is reflected in the deformation sensor optical fibres 162b and fed to the output optical fibres 20. Determination of the deformation of the deformable section 137 then proceeds similarly to that made for deformable section 37.

Figure 9A:
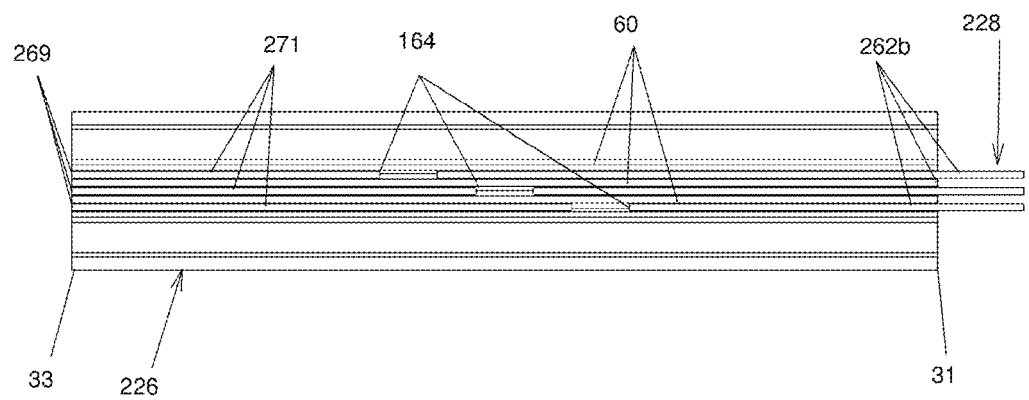
FIG. 9a, in a partial perspective view, illustrates another alternative deformable element.

In yet other embodiments of the invention, as seen in FIG. 9a the optically reflective surfaces 171 and deformation sensor optical fibres 162a are omitted in an alternative deformable element 226 and alternative deformation sensor 228. Instead, only the deformation sensor optical fibres 262b are provided in a respective one of the each fibre receiving grooves 60 that extend rectilinearly. The deformation sensor optical fibres 262b include an optically reflective coating. For example, the deformation sensor optical fibres 262b include a gold coated optical fibre segment 271 substantially adjacent the deformable element second end 33 and provided with a light reflective end surface 269 opposed to the deformation sensor gap 164. The gold coated optical fibre segments 271 reflect the light arriving at the light reflective end surface 269. Alternatively, the whole deformation sensor optical fibres 162b are gold coated.

Figure 10:
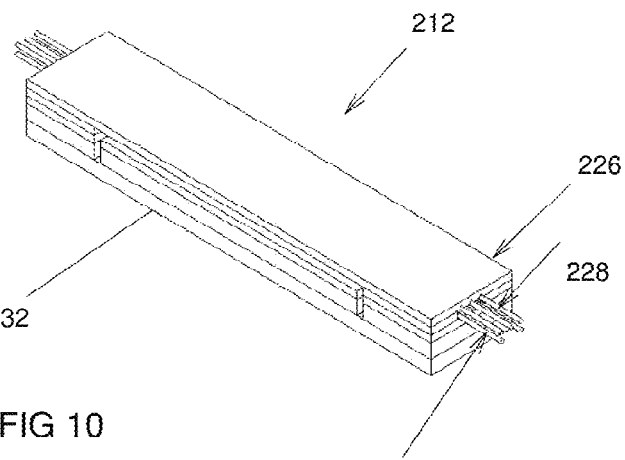
FIG. 10, in a perspective view, illustrates an alternative sensing element usable in the system shown in FIG. 1.

FIG. 10 illustrates an alternative sensing element 212. This sensing element 212 functions substantially similarly to the sensing element 12, but does not require the ferrules 48 and 50. Instead, all the optical fibres contained in the sensing element 212 are inserted in suitably shaped grooves and the various components of each the first and second spacing elements 241 and 243 are stacked directly on top of each other.

Figure 12:
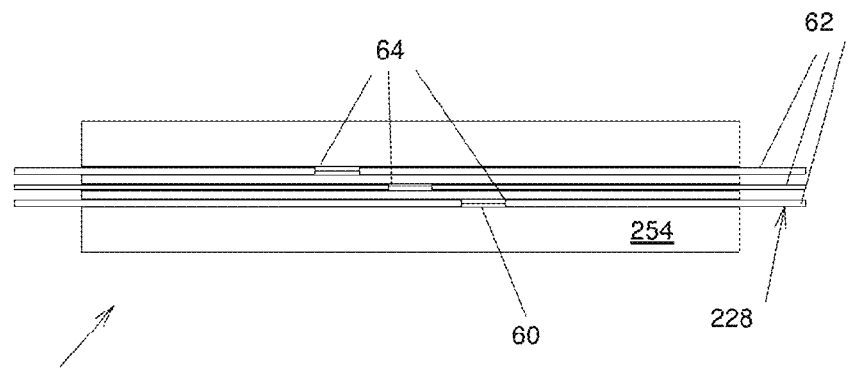
FIG. 12, in bottom plan view, illustrates a deformable element and deformation sensor part of the sensing element shown in FIG. 10.

More specifically, the sensing element 212 is similar to the sensing element 12 except that it includes an alternative deformable element 226, alternative mobile segments 236 and an alternative stationary segment 234. As seen in FIG. 12, the deformable element 226 is substantially similar to the deformable element 26, except that the support grooves 58 are omitted. Therefore, except for the fibre receiving grooves 60, the fibre receiving surface 254 of the deformable element 226 is substantially planar. Otherwise, the deformable element 226 and the deformation sensor 228 work substantially similarity to the corresponding structures in the sensing element 12.

Figure 11:
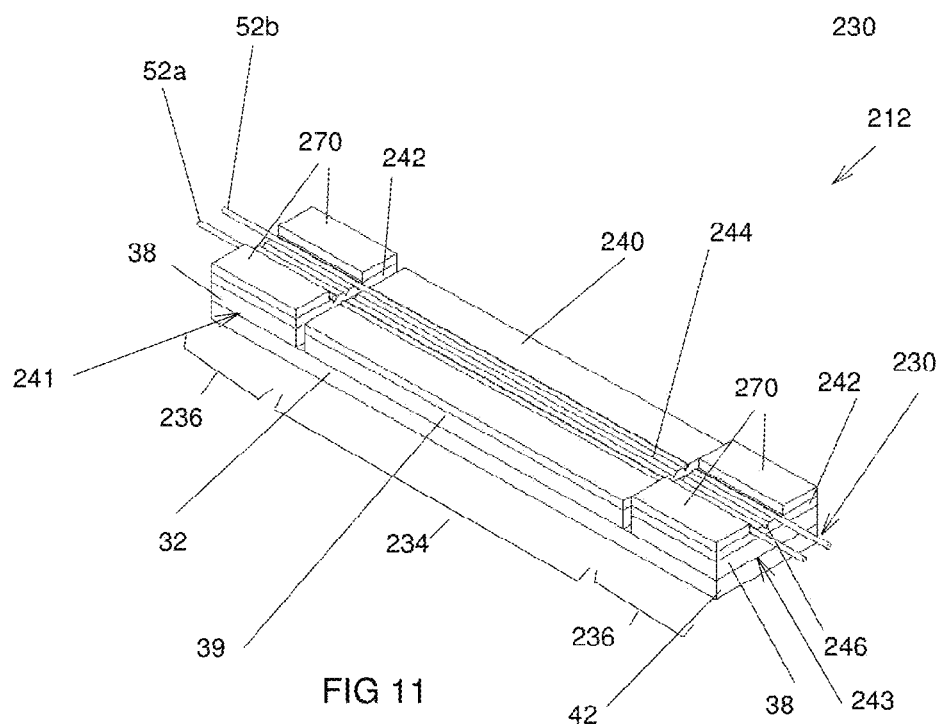
FIG. 11, in a perspective view with parts removed, illustrates the sensing element shown in FIG. 10.

Referring to FIG. 11, the stationary segment 234 and the mobile segments 236 include stationary and mobile optical element supports 240 and 242 respectively deprived of the support grooves 44 and 46. Instead, fibre receiving grooves 244 and 246 are provided respectively in the stationary and mobile optical element supports 240 and 242. The fibre receiving grooves 244 and 246 are shaped similarly to the fibre receiving grooves 60 of the deformable element 226 and are provided substantially in register therewith. This configuration allows for using a single mask to manufacture the fibre receiving grooves 244 and 246 and the fibre receiving grooves 60 when microfabrication techniques are used to manufacture the sensing element 212. Spacers 270 extend between the mobile optical element supports 242 and the deformable element 226 and are provided laterally outwardly with respect to the fibre receiving grooves 244 and 246. Therefore, instead of being transmitted through the ferrules 48, forces exerted onto the deformable element 226 are transmitted to the base 32 and the compressible elements 38 through the spacers 270. Otherwise, the principle on which the force sensor 230 is based is substantially similar to the principle on which the force sensor 30 is based and depends on changes in light transmission of optical fibres when the compressible elements 38 are compressed.

Figure 13:
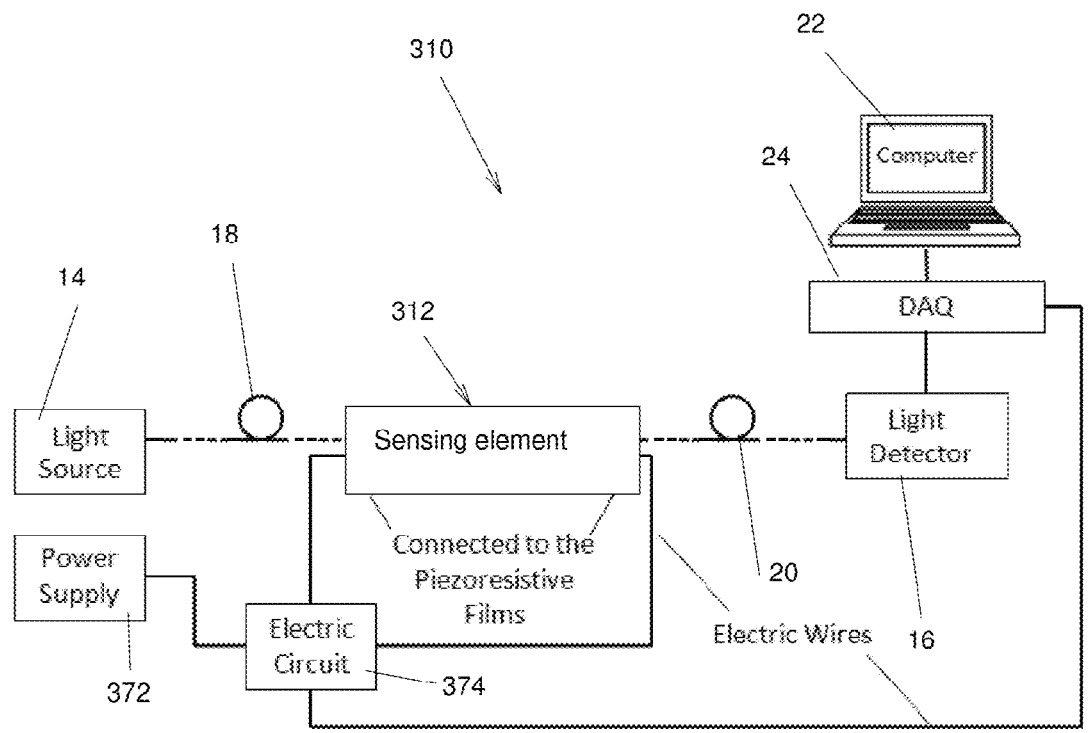
FIG. 13, in a schematic view, illustrates a system for sensing a mechanical property of a sample in accordance with an alternative embodiment of the present invention, the system including an alternative sensing element.

Referring to FIG. 13, there is shown an alternative system 310 for sensing and displaying softness and force, or other mechanical properties of the sample 25. The system 310 is substantially similar to the system 10 and only the differences between these two systems are described hereinbelow. The system 310 includes a power supply 372 and an electronic circuit 374. The power supply 372 provides power to an electrically powered force sensor 330, shown in FIG. 14, which feeds electrical signals to the electronic circuit 374. These electrical signals are indicative of the force exerted onto the force sensor 330 and the electronic circuit 374 is adapted for conveying this force information to the computer 22. Otherwise, deformation sensing is performed as been the system 10.

Figure 14:
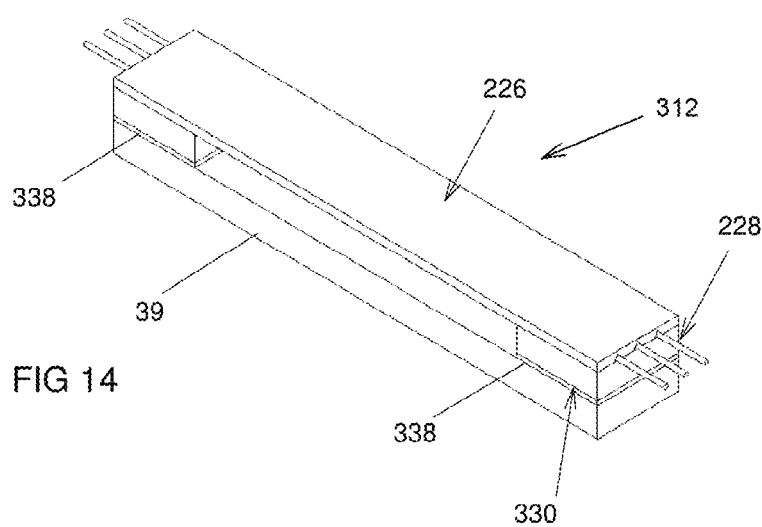
FIG. 14, in a perspective view, illustrates the sensing element part of the system shown in FIG. 13.

As seen in FIG. 14, an alternative sensing element 312 includes a pair of piezoresistive elements 338 that replace the compressible elements 38. Force sensing is effected by the piezoresistive elements 338 by measuring changes in resistance caused by compression of these piezoresistive elements 338. Therefore, the force sensing optical fibres 52a and 52b, and the ferrules 48 and 50 are omitted from the force sensor 330. For clarity reasons, wires that are used to receive the electrical signals provided by the piezoresistive elements 338 are not shown in FIG. 14, but the reader skilled in the art will readily appreciate which configurations wires would provide satisfactory signal acquisition. Also for example, the piezoresistive element is made of semiconductive polymer composites such as carbon-filled polyethylene films. As another alternative, instead of the piezoresistive element, piezoelectric elements such as Polyvinylidene Fluoride (PVDF) can be used.

All the above described deformation sensors 28 and force sensors 30 can be mixed together in any suitable manner to form the sensing elements 12. Also, in alternative embodiments of the invention, either of the deformation sensor 28 and force sensor 30 can be replaced by conventional deformation and force sensors.

In some embodiments of the invention, the sensing elements 12, 212 and 312 are manufactured using microfabrication technology and, for example, are mostly made out of silicon, except for the compressible elements 38 which are made out of a more compressible material, such as, for example, polydimethylsiloxane (PDMS), silicone-rubber, rubber, an epoxy, a rubber, or a polymer, among others.

The reader skilled in the art will readily appreciate that the above described force and deformation sensors 30 and 28 are usable independently from each other in alternative devices.

Although the present invention has been described hereinabove by way of preferred embodiments thereof, it can be modified, without departing from the spirit and nature of the subject invention as defined in the appended claims.

What is claimed is:

1. A sensing element for sensing a mechanical property of a sample defining a sample surface using a contact force exerted on said sensing element by said sample surface, said sensing element comprising:

a deformable element defining a deformable element first end and a substantially opposed deformable element second end, said deformable element defining a contact surface and a deformable section substantially in register with said contact surface between said deformable element first and second ends, said deformable section being deformable between an undeformed configuration and a deformed configuration, wherein said deformable section is in said undeformed configuration when no external forces are exerted on said contact surface and said deformable section is in said deformed configuration when said contact force is exerted on said contact surface;

a deformation sensor operatively coupled to said deformable section for sensing and quantifying a deformation of said deformable section between said deformed and undeformed configurations, said deformation sensor being an optical deformation sensor; and a force sensor operatively coupled to said deformable element for sensing said contact force exerted on said contact surface;

wherein said deformation sensor includes a deformation sensor interrupted optical waveguide defining a deformation sensor waveguide first segment, a deformation sensor waveguide second segment and a deformation sensor gap extending therebetween, said deformation sensor gap being provided substantially in register with said deformable section, said deformation sensor waveguide first and second segments being optically coupled to each other across said deformation sensor gap and secured to said deformable element with said deformation sensor waveguide first and second segments fixed with respect to said deformable section substantially adjacent said deformation sensor gap, wherein said deformation sensor waveguide first and second segments move relative to each other as said deformable section is moved between said undeformed and deformed configurations to vary optical coupling therebetween by at least one of relative translation or rotation of the deformation sensor waveguide first and second segments relative to each other;

whereby, when said contact and sample surfaces are abutted against each other and biased toward each other said contact force is created on said contact surface and sensed by said force sensor; and said deformable section achieves said deformed configuration, said deformed configuration being sensed and quantified by said deformation sensor.

2. The sensing element as defined in claim 1, wherein an optical coupling between an angle between longitudinal axes of said deformation sensor waveguide first and second segments substantially adjacent said gap varies as said deformable section is moved between said undeformed and deformed configurations.

3. The sensing element as defined in claim 1, wherein said deformable element defines a waveguide receiving surface opposed to said contact surface, said deformation sensor interrupted optical waveguide being secured to said waveguide receiving surface.

4. The sensing element as defined in claim 3, wherein
said deformation sensor interrupted optical waveguide is a deformation sensor optical fiber, said deformation sensor waveguide first and second segments being respectively a deformation sensor fiber first segment and a deformation sensor fiber second segment; and
said waveguide receiving surface defines a substantially elongated fiber receiving groove extending thereinto, said deformation sensor fiber first and second segments being provided in said fiber receiving groove.

5. The sensing element as defined in claim 4, wherein said deformation sensor waveguide first and second segments are bonded to said deformable element in said fiber receiving groove.

6. The sensing element as defined in claim 1, wherein
said deformation sensor waveguide first segment extends between said deformable element first end and said deformation sensor gap; and
said deformation sensor waveguide second segment extends between said deformable element second end and said deformation sensor gap.

7. The sensing element as defined in claim 1, wherein said deformation sensor waveguide first segment extends between said deformable element first end and said deformation sensor gap, and said deformation sensor waveguide second segment extends from said deformation sensor gap towards said deformable element second end and is provided with a light reflective end surface opposed to said deformation sensor gap.

8. The sensing element as defined in claim 1, wherein
said deformable element defines an auxiliary light guiding element provided between said deformation sensor gap and said deformable element second end;
said deformation sensor waveguide first segment extends between said deformable element first end and said deformation sensor gap;
said deformation sensor waveguide second segment extends between said deformation sensor gap and said auxiliary light guiding element;
said deformation sensor interrupted optical waveguide defines a deformation sensor waveguide third segment extending between said deformable element first end and said auxiliary light guiding element;
said auxiliary light guiding element optically couples said deformation sensor waveguide second and third segments.

9. The sensing element as defined in claim 8, wherein said auxiliary light guiding element includes a pair of mirrors configured for changing a light direction propagation of light incoming at said mirrors by about 180 degrees.

10. The sensing element as defined in claim 8, wherein said deformation sensor waveguide second and third segments are in a substantially parallel and spaced apart relationship relative to each other.

11. The sensing element as defined in claim 1, further comprising
a base, said base and said deformable element extending in a substantially parallel and spaced apart relationship relative to each other; and
a first spacing element extending between said base and said deformable element substantially adjacent said deformable element first end;
wherein said deformable element second end is movable with respect to said base.

12. The sensing element as defined in claim 1, further comprising
a base, said base and said deformable element extending in a substantially parallel and spaced apart relationship relative to each other;
a first spacing element extending between said base and said deformable element substantially adjacent said deformable element first end; and
a second spacing element extending between said base and said deformable element substantially adjacent said deformable element second end;
wherein in said undeformed configuration, said deformation sensor waveguide first and second segments have substantially coaxial optical axes.

13. The sensing element as defined in claim 1, wherein said deformation sensor includes an other deformation sensor interrupted optical waveguide defining an other deformation sensor waveguide first segment, an other deformation sensor waveguide second segment and an other deformation sensor gap extending therebetween, said other deformation sensor gap being provided substantially in register with said deformable section, said other deformation sensor waveguide first and second segments being optically coupled to each other across said deformation sensor gap and secured to said deformable element with said other deformation sensor waveguide first and second segments fixed with respect to said deformable section substantially adjacent said deformation sensor gap, whereby optical coupling between said other deformation sensor waveguide first and second segments varies as said deformable section is moved between said undeformed and deformed configurations through changes in alignment between said other deformation sensor waveguide first and second segments.

14. The sensing element as defined in claim 13, wherein
said deformation sensor interrupted optical waveguide and said other deformation sensor interrupted optical waveguide extend substantially parallel to each other in a laterally spaced apart relationship relatively to each other; and
said deformation sensor gap and said other deformation sensor gap are longitudinally offset with respect to each other.

15. The sensing element as defined in claim 1, wherein said force sensor is an optical force sensor, said force sensor includes a force sensor interrupted optical waveguide defining a force sensor waveguide first segment, a force sensor waveguide second segment and a force sensor gap extending therebetween, said force sensor waveguide first segment extending through said first spacing element and being fixed relative thereto substantially adjacent said force sensor gap, said force sensor waveguide second segment being supported by said base and fixed relative thereto substantially adjacent said force sensor gap, said force sensor waveguide first and second segments being optically coupled to each other across said force sensor gap, said first spacing element including a first support resiliently deformable section provided between said base and said force sensor optical waveguide first segment, whereby, when said first support resiliently deformable section is compressed, said force sensor waveguide first segment is moved relative to said force sensor waveguide second segment, which changes optical coupling between said force sensor waveguide first and second segments.

16. The sensing element as defined in claim 15, wherein said force sensor interrupted optical waveguide is a force sensor optical fiber, said force sensor waveguide first and second segments being respectively a force sensor fiber first segment and a force sensor fiber second segment, said force sensor fiber first and second segments being inserted respectively through a first ferrule and a second ferrule, said first ferrule extending through said first spacing element and said second ferrule being supported by said base.

17. The sensing element as defined in claim 15, further comprising a second spacing element extending between said base and said deformable element, said first and second spacing elements being spaced apart from each other and respectively provided substantially adjacent said deformable element first and second ends.

18. The sensing element as defined in claim 1, wherein said force sensor includes a piezoresistive or a piezoelectric element provided between said first spacing element and said base.

19. A system for measuring a mechanical property of a sample defining a sample surface using a contact force by said sample surface, said system comprising:
    the sensing element as defined in claim 1;
    a light source optically coupled to said deformation sensor waveguide first segment opposed to said deformation sensor gap for emitting a source light in said deformation sensor waveguide first segment;
    a light detector optically coupled to said deformation sensor waveguide second segment opposed to said deformation sensor gap for detecting an intensity of light received from said deformation sensor waveguide second segment;
    a controller operatively coupled to said light detector for receiving said intensity of light received from said deformation sensor waveguide second segment when said source light is emitted in said deformation sensor waveguide first segment and computing a deformation of said deformable section using a power loss of said source light across said sensing element; and
    an output element for outputting said deformation.

20. A system for measuring a mechanical property of a sample defining a sample surface using a contact force exerted on said sensing element by said sample surface, said system comprising:
    the sensing element as defined in claim 15;
    a light source optically coupled to said force sensor waveguide first segment opposed to said force sensor gap for emitting a source light in said force sensor waveguide first segment;
    a light detector optically coupled to said force sensor waveguide second segment opposed to said force sensor gap for detecting an intensity of light received from said force sensor waveguide second segment;
    a controller operatively coupled to said light detector for receiving said intensity of light received from said force sensor waveguide second segment when said source light is emitted in said force sensor waveguide first segment and computing said contact force exerted on said contact surface using a power loss of said source light across said sensing element; and
    an output element for outputting said contact force.

* * * * *